(12) United States Patent
Hastings et al.

(10) Patent No.: US 7,383,742 B2
(45) Date of Patent: Jun. 10, 2008

(54) SEPTUM LEAK DETECTOR

(75) Inventors: Mitchell Robert Hastings, Rancho Murieta, CA (US); Michael Richard Saunders, Orangevale, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 209 days.

(21) Appl. No.: 11/313,391

(22) Filed: Dec. 21, 2005

(65) Prior Publication Data
US 2007/0151367 A1 Jul. 5, 2007

(51) Int. Cl.
*G01F 15/00* (2006.01)
(52) U.S. Cl. .................................................. 73/861.77
(58) Field of Classification Search ............... 73/23.42, 73/23.1, 863.22, 863.23; 436/161; 364/550
See application file for complete search history.

(56) References Cited

U.S. PATENT DOCUMENTS

| | | | | |
|---|---|---|---|---|
| 4,414,839 A | * | 11/1983 | Dilley et al. ................. | 73/23.4 |
| 4,766,557 A | * | 8/1988 | Twerdochlib ................ | 702/51 |
| 4,962,042 A | * | 10/1990 | Morabito et al. ........... | 436/161 |
| 6,951,147 B2 | * | 10/2005 | Call et al. ................ | 73/863.22 |

* cited by examiner

*Primary Examiner*—Jewel Thompson

(57) ABSTRACT

A gas flow sensor receives a low-volume gas flow to be measured in a selectively sealed chamber. A flow rate signal is generated using a measuring device in response to the received gas flow. The flow rate signal is converted into a desired format for purposes of storage, control, and/or display.

29 Claims, 2 Drawing Sheets

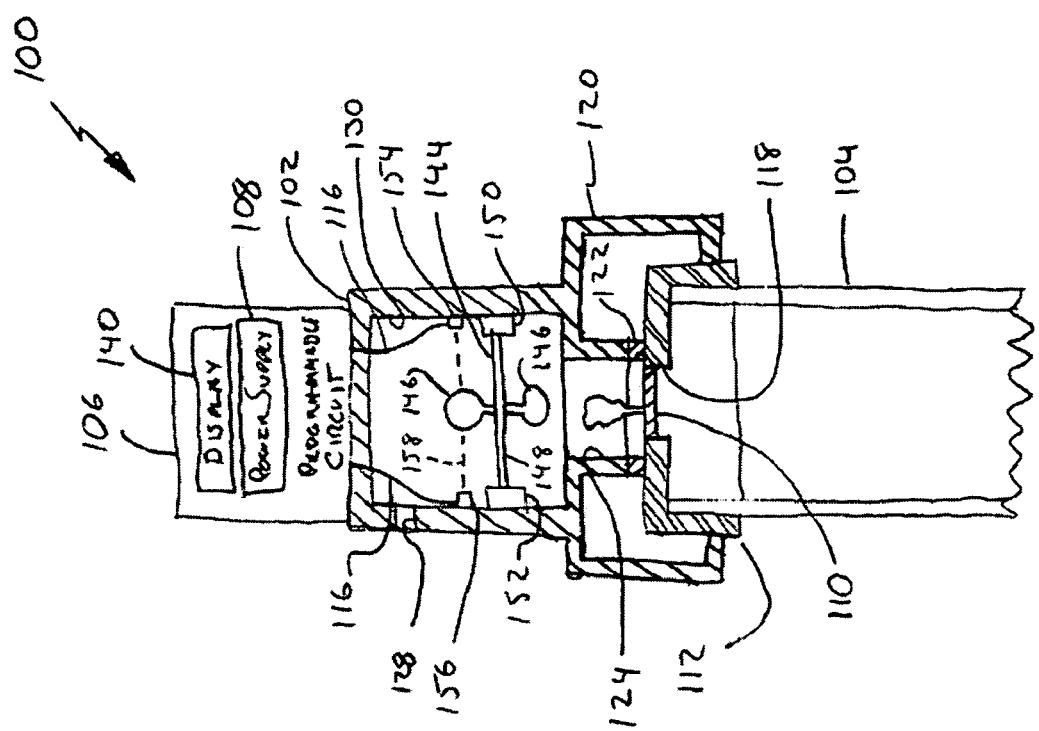

SEPTUM LEAK DETECTOR

BACKGROUND

Conventional devices for accurately measuring (and/or manipulating) various chemical compositions usually maintain an enclosed environment. The enclosed environment helps to ensure that the various chemical compositions are not changed or otherwise affected by the environment. For example, gas chromatography (GC) is a technique used to separate and measure volatile organic compounds. A gas chromatograph typically includes an injector port that is used to introduce a sample into the enclosed environment of the gas chromatograph. The injector port typically includes a septum through which the sample is injected. The septum is typically made of rubber and rubber mixtures containing substances such as silicone, plasticizers, organometallics, and the like, which help the septum to reseal properly. However, the septum degrades over time and with use.

The service life of a GC inlet septum is highly unpredictable under all but the most controlled conditions. Even small septum leaks (e.g., as low as 0.1 ml per minute) allow oxygen to enter the flow path. The introduced oxygen can damage sensitive parts in the GC flow path, including degradation of liner deactivations, degradation of GC column stationary phase, and oxidation of sensitive detector parts (such as mass spectrometer detectors). Further, degradates from liner and column phases often interfere with detection of analytes, foul detectors, and the like. Thus, the intrusion of oxygen (especially through a degraded septum) renders the analysis of the sample less effective, and increases costs and frequency of maintenance of the GC.

A GC septum is replaced in accordance with a chosen maintenance period for the purpose of lowering the chances of intrusion of oxygen into the GC. However, the GC is unavailable for use while the septum is being replaced. The time required to replace a septum is typically from around 30 minutes to around four hours before systems using the GC septum are re-equilibrated. Maintaining the GC septum, then, poses a dilemma: too frequent changes of the septum result in expensive downtime and too infrequent changes of the septum result in intrusion of oxygen with the resulting decrease in the life of oxygen-sensitive flow path parts.

SUMMARY

In general terms, this patent relates to isolating a septum from an external environment and detecting a physical characteristic of gas that leaks through the septum.

One aspect is an apparatus for measuring gas flow through a septum. The apparatus comprises a housing defining a chamber and an opening. A sensor is positioned within the housing. The sensor is responsive to a gas flowing though the septum, through the opening, and into the chamber.

Another aspect is a method of detecting leaks in a septum of a vessel. The method comprises positioning a housing proximal to a septum, the housing defining a chamber and an opening; substantially isolating the chamber from an external environment; and upon gas leaking through the septum, detecting at least one physical characteristic of the gas.

BRIEF DESCRIPTION OF THE DRAWINGS

FIG. 3 is a cross sectional view of an alternative embodiment of the flow rate detector illustrated in FIG. 1 in which the sensor arrangement includes a rotary vane.

DETAILED DESCRIPTION

Figure 1:
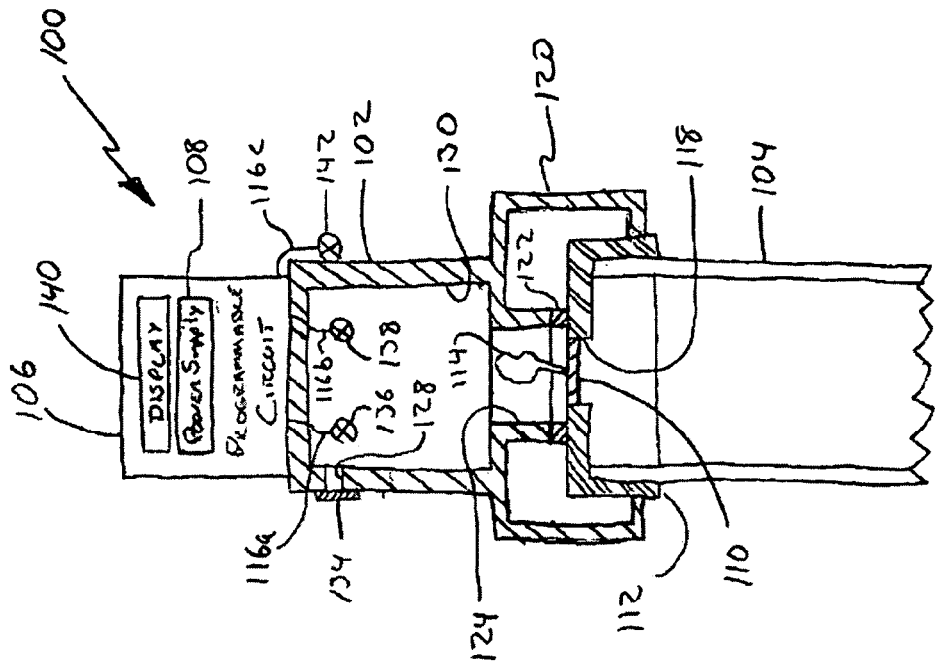
FIG. 1 is a cross-sectional view of a flow rate detector having a sensor arrangement.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

Chromatography involves the separation of a mixture of compounds (e.g., solutes) into separate components. Separating the sample into individual components allows identification and measurement of the various sample components. Gas chromatography (GC) is suitable for analyzing 10-20% of known compounds. To be suitable for GC analysis, a compound typically should have sufficient volatility and thermal stability. If all or some molecules of a compound are in the gas or vapor phase at around 400-450° C. (or below), and do not decompose at these temperatures, the compound can usually be analyzed using GC.

A GC system typically comprises an injector, a column, and a detector. In operation, one or more high purity gases are supplied to the GC at the injector. One of the gases (called the carrier gas) flows into the injector, through the column and then into the detector. A sample is introduced into the injector using, for example, a syringe or an exterior sampling device. The injector is typically heated to 150-250° C. for the purpose of causing the volatile sample solutes to vaporize.

The vaporized solutes are transported into the column by the carrier gas. The column is typically arranged within a temperature-controlled oven. The solutes travel through the column at a rate in accordance with physical properties of the solutes, the temperature, and composition of the column. The various solutes typically travel through the column at rates that vary in accordance with differing physical properties of the solutes. Typically the fastest moving solute exits ("elutes") the column first, and is followed by the remaining solutes in an order that is associated with physical properties of the different kinds of solutes. As each solute elutes from the column, the solute enters the detector, which is typically heated. An electronic signal is generated upon interaction of the solute with the detector. Signal parameters are recorded by a data system and typically plotted over time to produce a chromatogram.

In an example GC system, a capillary GC column comprises a tubing and stationary phase. A thin film (0.1-10.0 µm) of a high molecular weight, thermally stable polymer is typically coated onto the inner wall of small diameter (0.05-0.53 mm I.D.) tubing to provide a polymer coating (that is associated with the stationary phase). Gas flows through the tubing and is called the carrier gas (and is associated with the mobile phase).

Upon introduction into the column, solute molecules typically distribute between the stationary and mobile phases. The molecules in the mobile phase are carried down the column; the molecules in the stationary phase are temporarily immobile and as such do not move down the column. As the molecules in the mobile phase move through the column, some of them eventually collide with and re-enter the stationary phase. During the same time span, some of the solute molecules leave the stationary phase and enter the mobile phase. This often occurs thousands of times for each solute molecule as it passes through the column.

The molecules corresponding to a specific compound usually travel through the column at nearly the same rate and appear as a band of molecules (called the sample band) at the detector. Avoiding an overlap between adjacent sample bands as they exit the column can be accomplished by having each sample band travel at a different rate and by minimizing the width of the sample band. The rate at which each sample band moves through the column is a function of the structure of the compound, the chemical structure of the stationary phase, and the column temperature. The width of the sample band is dependent on the operating conditions and the dimensions of the column. An unknown substance can be identified by comparing the retention and peak size with the retention and peak size of a known substance as long as the retention and/or peak sizes are not the same. Accordingly, peak co-elution can be minimized by selecting a proper column and the operating conditions.

FIG. 1 illustrates an exemplary embodiment of a septum leak detector 100. The exemplary embodiment engages a septum nut 112 that defines an opening 118 and is fixed to a vessel 104 for holding a gaseous sample. Septum 110 is attached to and covers the opening 118 in septum nut 112. The septum nut 112 attaches to the vessel 104 in any conventional manner. Examples can include threading to the vessel or fitting into and frictionally engaging the vessel such as a stopper.

Septum nut 112 and septum 110 seal the vessel 104 and provide an environmentally closed system (such as in a gas chromatograph) that contains flowing gases. In various applications, the septum 110 provides an injection site for introducing substances to the environmentally closed system. However, the septum 110 develops leaks 114 over time as the material forming the septum 110 degrades because of circumstances such as oxidation in the presence of oxygen and repeatedly traversing the septum with a needle (as in during injections). Although a particular septum nut 112 and septum 110 arrangement is illustrated, septum leak detectors within the scope of this document can be used with alternative structures of septums and alternative retaining structures for the septums.

In the exemplary embodiment, the septum leak detector 100 includes a housing 102 having a base portion 120 and defining a chamber 130, a seal 122, and a sensor arrangement 132. The base portion 120 is annular and defines an inner passage 124 that is open to the chamber 130. An annular seal 122 such as an o-ring is attached to the base portion and circumscribes the inner passage 124. The base portion 120 is configured to be removably attached to the septum nut 112 and/or vessel 104. In various embodiments, the base portion 120 can be attached to the septum nut 112 with different mechanisms such as threads, a frictional fit, clips, clamps, or the like.

The sensor arrangement 132 can be any type of sensor that responds to one or more physical characteristics of gas so that gas within the chamber gas can be quantified. Examples of physical characteristics include temperature, the number of moles, pressure within a chamber, flow rate, and the like. Some embodiments calculate the flow rate of gas based on measured physical characteristics or by directly measuring the flow rate. In the exemplary embodiments disclosed herein, for example, the flow rate of gas is determined from calculating the number of moles of gas or from measuring the rate at which the gas rotates a vane. Yet other embodiments might determine whether a leak exists by analyzing a physical characteristic other than flow rate.

When the base portion 120 is attached to the septum nut 112, the annular seal 122 engages the septum nut, circumscribes the septum 110, and seals any space between the base portion and the septum nut 112. The septum 110 is in fluid communication with the chamber 130 through the inner passage 124 of the base portion 120. The seal 122 isolates the chamber 130, inner passage 124 of the base portion 120, and septum 110 from the external environment and substantially prevents any gas associated with leak 114 from leaking to the environment, and likewise substantially prevents entry of any environmental gas into the chamber 130. Although an o-ring type of seal is illustrated, other embodiments can include any type of seal and related structure that isolates the septum 110, inner passage 124, and chamber 130 from the external environment.

The leak detector 100 can be attached to the nut 112 for a single measurement and then immediately removed. Alternatively, the leak detector 100 can be mounted on the septum nut 112 and left there for convenience, for repeated testing for leaks in the septum, or for continuous testing for leaks in the septum 110.

In the exemplary embodiment, a sensor arrangement 132 that responds to the leaking gas is positioned within the chamber 130 and is in electrical communication via leads 116 with programmable circuit 106 that include a display 140. The programmable circuit 106 receives a signal generated from the sensor arrangement 132, determines a flow rate and displays the flow rate on the display 140. The exemplary embodiment includes any type of conventional programmable circuit configured to processes signals from the sensor arrangement 132 and generates a display in response thereto. Other embodiments could include nonprogrammable circuits that are responsive to the sensor arrangement.

In various embodiments, the programmable circuit 106 and display 140 are physically attached to base portion 120. In other embodiments, the programmable circuit 106 and display 140 are physically separated from base portion 120, and are in electrical communication with the sensor arrangement 132 via a data link that communicates according to any suitable communication protocol and can be either wired or wireless (e.g., radio frequency, infrared, and acoustic). The display 140 can be a liquid crystal display, a CRT, light emitting diodes (LED's), or any other component or device that can communicate information. The programmable circuit 106 also includes a power supply 108. The power supply 108 can provide power for any active circuitry used in the sensor arrangement 132.

In use, the sensor arrangement 132 responds to the gas 114 and provides a signal to the programmable circuit 106. The programmable circuit 106 in the exemplary embodiment processes the signal and determines the flow rate of gas. In the exemplary embodiments, the programmable circuit 106 determines the flow rate of gas by either measuring it directly or by calculating the leak rate in real-time by measuring a physical characteristic of the gas and using this information to calculate the flow rate using any of desired units of measurement such as moles per second, mils per second, and the like. In various embodiments, the programmable circuit 106 can present the information and generate warning signals. For example, if an LCD or CRT display is used, the display 140 can present the calculated flow rate for the user to read.

In other embodiments, the programmable circuit 106 is programmed with a failure threshold value that indicates the failure point for a septum. In these embodiments, the programmable circuit 106 compares the calculated flow rate to the threshold value and generates a failure signal if the calculated flow rate reaches or exceeds the failure threshold value. In yet other embodiments, the programmable circuit 106 is programmed with a warning threshold value that indicates the flow rate of gas through the septum 110 is approaching the failure point, but has not yet failed. In this embodiment, the programmable circuit 106 compares the calculated flow rate to the warning and failure threshold values and generates a warning signal if the flow rate reaches or exceeds the warning threshold value and a failure signal if the flow rate reaches or exceeds the failure threshold value.

The failure and warning signals can take a variety of forms depending on the embodiment. Examples include certain words (e.g., "failure" or "warning") or other indicia if the display is an LCD or CRT. In other possible embodiments, the failure and warning signals are generated by illuminating LEDs. For example, a red LED could be used for a failure signal and a yellow LED can be used for a warning signal.

As discussed in more detail herein, the programmable circuit 106 determines the flow rate of gas leaking through the septum 110 in any appropriate units of measurement such as moles per second, milliliters per second, and the like. Furthermore, the sensor arrangement 132 and programmable circuit 106 are capable of measuring gas leaks in the range of about 0.01 ml to about 2 ml per minute with an accuracy of about 15% or better. In other embodiments, the sensor and programmable circuit 106 are capable of measuring gas leaks in the range of about 0.6 ml per minute to about 6 ml per minute. These ranges and level of accuracy have several advantages over conventional methods.

For example, soap bubble flow meters rely on the creation of a soap bubble in the flow in a tube connected to a flow source. The soap bubble flow meter typically does not measure accurately below about 1-5 mL/min due in part to variations in water and bubble pressure and other inaccuracies in estimating the volume of the bubble.

Acoustic displacement technology measures by exposing a flexible membrane to the force created by the flow path in an open system. The technology is designed for an open system (which allows introduction of contaminants), requires frequent recalibration to maintain accuracy, and typically does not measure accurately below about 1.0 mL/min.

Acoustic flowmeters measure the phase shift of a sound wave propagating though a duct containing a flowing gas, where the gas (and the equation of the gas state) is known. Acoustic phase measurements, thus, require "before-hand" (i.e., a priori) knowledge of the composition of the gas to be measured and typically do not measure accurately below about 0.1 mL/min.

In some possible embodiments, a user can optionally select a desired format for the output generated by the programmable circuit 106 and displayed on the display 140. Examples of formats that the user might be able to select in these embodiments include whether to display the flow rate, a failure signal, and a warning signal, or any combination thereof. The user also might be able to select the units of measurement for displaying the flow rate.

Figure 2:
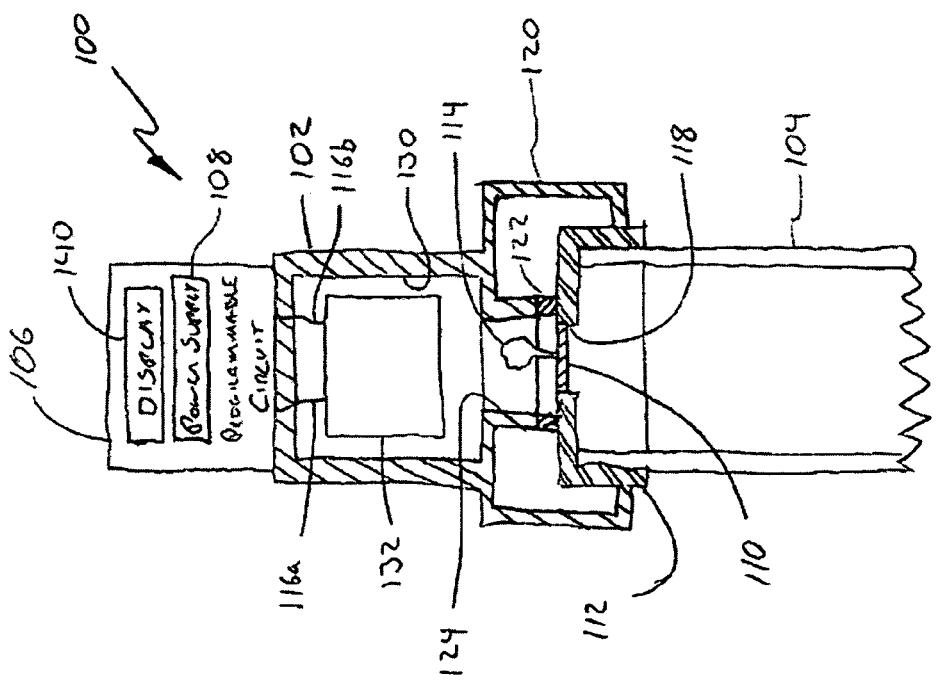
FIG. 2 is a cross sectional view of the flow rate detector illustrated in FIG. 1 in which the sensor arrangement includes pressure and temperature sensors.

FIG. 2 illustrates an exemplary embodiment of a septum leak detector 100 that includes a housing 102 defining a chamber 130 and having a base portion 120, a seal 122, a sensor arrangement 132, and programmable circuit 106 with a display 140. The housing 102 includes a port 128 that the user can selectively open and close with a plug 134. When the port 128 is open, it provides an opening between the chamber 130 and the atmosphere external to the housing 102.

The sensor arrangement 132 includes an internal temperature sensor 136 and an internal pressure sensor 138 positioned within the chamber and in electrical communication with the programmable circuit. An external pressure sensor 142 is located on the outer surface of the housing 102 and is also in electrical communication with the programmable circuit.

In operation, the housing 102 is attached to a septum nut 112 for testing the septum 110. After the housing 102 is attached to the septum nut 112, the port 128 is opened to equalize internal and external pressures associated with chamber 130. As gas leaks through (i.e., traverses) the septum 110, the pressure and temperature of chamber 130 increases in accordance with the Ideal Gas Equation:

$$PV=nRT \quad (1)$$

where P is the pressure internal to the camber 130, V is the volume of the chamber 130 and the inner passage 124 of the base portion 120, n is the quantity of gas in the chamber 130 expressed in moles, R is the gas constant, and T is the temperature in the chamber 130. The internal pressure and temperature sensors 138 and 136 generate pressure and temperature signals, respectively, corresponding to the pressure and temperature within the chamber 130 and input these signal to the programmable circuit 106. The programmable circuit 106 them uses the ideal gas equation to calculate the quantity of gas in the chamber 130 at least two different points in time and uses this information to calculate the flow rate using the equation:

$$F=n/\Delta t \quad (2)$$

where F is the flow rate of gas in moles per second, n is the number of moles calculated according to the ideal gas equation (Equation 1), $\Delta t$ is the lapsed time between the start of the measurement and the moment that measurement of the internal pressure and temperature is concluded. Depending on the embodiment as described herein, the calculated flow rate is displayed on the display 140. In other embodiments, the programmable circuit 106 compares the calculated flow rate to a predetermined warning threshold value and/or a predetermined failure threshold value and generates warning and/or failure signals and displays as described above.

For repeated measurements (as in an industrial manufacturing process), the port is opened to equalize pressures between the interior and exterior of chamber 130, and then closed again, which allows successive measurements to be made.

In various embodiments, the internal pressure 138, internal temperature 136, and external pressure 142 sensors are used in different ways to determine flow rates. In one embodiment, the step of re-equalizing the pressure can be replaced (or combined with) with the step of "re-zeroing" the measurements made with the internal pressure 138 and internal temperature 136 sensors. The internal pressure 138 and temperature sensors 136 can be re-zeroed by considering a previous set of measurements to be a reference point from which a subsequent measurement set is used to determine flow rate.

In an alternate embodiment, the external pressure sensor 142 can be used as reference point to determine (and/or verify) increases in pressure in the interior of the chamber 130. For example, the exterior pressure sensor 142 can be used to determine the instantaneous pressure difference (by taking the difference of the interior 138 and exterior pressure sensors 142), which can be further used to validate the calculation of the change in internal pressure (over time) made by successive measurements using the interior pressure sensor 138.

In another alternate embodiment, the port 238 is not opened to equalize the internal chamber pressure and the external pressure. Instead, for example, septum leak detector 100 itself can be removed from septum nut 112, which equalizes the pressure.

Septum leak detector 100 is used to calculate leak rates from a septum 110 under which there is a pressure of either ambient or vacuum below ambient pressure. Experimental test results have shown septum leak detector 100 is capable of measuring leaks between 0.01-2.0 ml per minute, with a plus or minus 15 percent accuracy or better. The volume parameter (from the Ideal Gas Equation) is determined by the volume of chamber 130 and the volume, if any, provided by septum 110 recessed within (or protruding from) septum nut 112.

FIG. 3 illustrates another exemplary embodiment of a septum leak detector that includes a housing 102 defining a chamber 130 and having a base portion 120, a seal 122, a sensor arrangement 132, and programmable circuit 106 with a display 140. In this embodiment, the sensor arrangement 132 includes a rotary vane 144 having vane members 146 disposed radially about a shaft 148. Vane members 146 are configured to move and rotate the shaft 148 in response to the gas flow from leak 114 exerting a force against them.

The shaft 148 of rotary vane 144 is captivated by "frictionless" bearings 150 and 152. Frictionless bearings 150 and 152 impart no substantial static friction to the shaft 148 of rotary vane 144. The lack of substantial static friction allows the rotary vane 144 to begin rotating without the gas flow from the gas leak 114 having to overcome the static friction that is initially present when the shaft 148 is not rotating. The frictionless bearings 150 and 152 comprise permanent magnets and/or electromagnets that draw power from the power supply 108 in the programmable circuit 106.

The rotary vane 144 also comprises a light source 156 positioned on one side of the vane members 146 and a light sensitive transducer 154 on the opposite side of the vane members 146. The light source 156 shines a light beam 158 onto the light sensitive transducer 154, which generates a signal in response thereto and inputs that signal into the programmable circuit 106. As the vane shaft 148 rotates, the vane members 146 repeatedly break the light beam 158 thereby interrupting the signal input from the light-sensitive transducer 144 to the programmable circuit 106. The programmable circuit 106 uses the time between successive pulses in the signal (and the angles subtended by the vane members 146 about the axis of rotation) to determine the angular speed of the rotation of rotary vane 144.

In operation, the housing 102 is attached to the septum nut 112 for testing the septum 110. The port 134 is open to exhaust the gas flowing through chamber 130 so that a substantial back pressure does not result within chamber 130 after the leak detector 100 is attached. A substantial amount of back pressure is a pressure that builds up in the chamber 130 and impedes the flow of gas leaking through septum 110, which adversely affects accuracy of the measurements. Some embodiments also include a pressure relief valve (not shown) in the wall of the housing 102 to protect rotary vane 144. The pressure relief valve opens and further vents the chamber 130 if pressure within the chamber exceeds a predetermined level.

As gas from the gas leak 114 flows through the chamber 130 it exerts a force against the vane members 146 and causes the rotary vane 144 to rotate and periodically interrupt the light traveling from the light source 156 to the light-sensitive transducer 154. In turn, the signal from the light-sensitive transducer 154 to the programmable circuit 106 is repeatedly interrupted and the programmable circuit 106 determines the length of time for each interruption. The programmable circuit 106 uses this length of time for the interruption to determine the angular velocity of the rotary vane 144. The angular velocity of the rotary vane 144 can be determined, for example, by comparing the rate of interruptions with the angular displacement (about the axis of rotation) of the vane members 146.

The programmable circuit 106 then determines the rate of the gas flow through the septum 110. The rate of the gas flow can be determined, for example, by correlating the measured angular velocity with stored empirical measurements made using a similar rotary vane sensor arrangement. A lookup table can be addressed using the angular velocity as an index and thereby obtaining the gas rate for the indexed angular velocity. Rates falling between intermediate index values can be determined by interpolation of values (such by using linear interpolation, least squares, curve fitting, and the like). Gas flow rates can be displayed in any convenient form, including moles per second, mils per second, and the like. In various embodiments as described herein, the programmable circuit 106 displays the flow rate of gas, generates a failure signal, and/or generates a warning signal.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. An apparatus for measuring gas flow through a septum, the apparatus comprising:
   a housing defining a chamber and an opening into the chamber, the opening being positionable adjacent to and in facing relation with the septum;
   a sensor positioned within the housing, the sensor responsive to a gas flowing though the septum, through the opening, and into the chamber.

2. The apparatus of claim 1 wherein the sensor includes a pressure sensor.

3. The apparatus of claim 2 wherein the sensor further includes a temperature sensor, wherein the sensor is arranged in a gas chromatography system.

4. The apparatus of claim 3 further comprising a circuit in electrical communication with the pressure sensor and the temperature sensor, the circuit programmed to determine the change in moles of gas over a predetermined period of time, the moles of gas being calculated according to the equation: $PV=nRT$ wherein P is pressure of gas within the chamber, V is the volume of the chamber, n is moles of gas in the chamber, R is a constant, and T is the temperature in the chamber.

5. The apparatus of claim 2 wherein the housing further includes a port and a cap arranged to selectively open and close the port.

6. The apparatus of claim 1 wherein the sensor includes a vane rotatably mounted within the chamber.

7. The apparatus of claim 6 further comprising a circuit, the circuit configured to determine the angular velocity of the vane.

8. The apparatus of claim 7 wherein:
the vane includes at lease one radially orientated member; and
the circuit includes a light source positioned on one side of the at least one radially orientated member and a light-sensitive transducer on the opposite side of at least one radially orientated member.

9. A sensor for measuring a gas flow, the sensor comprising:
a chamber having an initial temperature and an initial pressure, wherein the chamber is configured to receive a gas flow to be measured, and wherein the initial pressure and temperature increase in response to the received gas flow;
a first pressure sensor that is arranged to measure pressures that are associated with the chamber and to provide a first pressure signal in response;
a temperature sensor that is arranged to measure temperatures that are associated with the chamber and to provide a temperature signal in response; and
a computer that is configured to calculate a flow amount in response to receiving the first pressure and temperature signals.

10. The sensor of claim 9 wherein the amount is calculated in accordance with the Ideal Gas Equation.

11. The sensor of claim 9 further comprising an exhaust port that is configured to selectively open to equalize pressures of the chamber.

12. The sensor of claim 11 wherein pressures of the chamber are equalized with an external pressure before calculating an amount of gas in the chamber, wherein the amount of gas is in units of one of moles and volume, and wherein the amount of gas is calculated when temperatures of the chamber reach a selected temperature that is greater than the initial temperature.

13. The sensor of claim 11 wherein pressures of the chamber are equalized before calculating an amount of gas in the chamber, wherein the amount of gas is in units of one of moles and volumetric, and wherein the amount of gas is calculated when pressures of the chamber reach a selected pressure that is greater than the initial pressure.

14. The sensor of claim 9 further comprising a second pressure sensor that is arranged to measure an ambient pressures outside of the chamber and to provide a second pressure signal in response such that the second pressure signal is configured to be used by the computer to calculate the flow amount.

15. A sensor for measuring a gas flow, the sensor comprising:
a chamber that is configured to receive the gas flow;
a rotary vane positioned within the chamber that is configured to generate a gas flow signal in response to the gas flow through the chamber, wherein the rotary vane comprises substantially frictionless bearings; and
a computer that is configured to calculate a flow amount in response to the gas flow signal from the rotary vane.

16. The sensor of claim 15 wherein the substantially frictionless bearings are magnetic.

17. The sensor of claim 16 wherein the substantially frictionless bearings are electromagnetic.

18. The sensor of claim 17 wherein the rotary vane comprises an optical sensor that is configured to sense the angular speed of the rotation of the rotary vane.

19. The sensor of claim 18 wherein the sensor is removed from the gas flow between measurements of the gas flow.

20. The sensor of claim 18 wherein the computer is further configured to display the calculated flow amount.

21. A method for measuring gas flow though a septum, the method comprising:
providing a housing defining a chamber and an opening into the chamber; providing a sensor positioned within the chamber, the sensor being responsive to gas flowing into the chamber;
positioning the opening adjacent to and in facing relation with the septum thereby allowing gas flowing though the septum to flow through the opening, and into the chamber; and
measuring the gas flow into the chamber using the sensor.

22. The method of claim 21 wherein the sensor includes a pressure sensor and a temperature sensor.

23. The method of claim 21 further comprising arranging the sensor in a gas chromatography system.

24. The method of claim 23 further comprising determining the change in moles of gas over a predetermined period of time, the moles of gas being calculated according to the equation: $PV=nRT$ wherein P is pressure of gas within the chamber, V is the volume of the chamber, n is moles of gas in the chamber, R is a constant, and T is the temperature in the chamber.

25. The method of claim 22 wherein the housing further includes a port and a cap arranged to selectively open and close the port.

26. The method of claim 21 wherein the sensor includes a vane rotatably mounted within the chamber.

27. The method of claim 26 further comprising using an electronic circuit configured to determine the angular velocity of the vane.

28. The method of claim 27 further comprising positioning a light source on one side of the at least one radially orientated member of the vane and positioning a light-sensitive transducer on the opposite side of at least one radially orientated member of the vane.

29. The apparatus of claim 1, wherein the sensor is responsive to a gas flow comprising a range of from about 0.01 ml per second to about 0.1 ml per second.

* * * * *

UNITED STATES PATENT AND TRADEMARK OFFICE
CERTIFICATE OF CORRECTION

PATENT NO. : 7,383,742 B2  Page 1 of 1
APPLICATION NO. : 11/313391
DATED : June 10, 2008
INVENTOR(S) : Hastings et al.

It is certified that error appears in the above-identified patent and that said Letters Patent is hereby corrected as shown below:

In column 8, line 47, in Claim 1, delete "though" and insert -- through --, therefor.

In column 9, line 5, in Claim 8, delete "lease" and insert -- least --, therefor.

In column 10, line 16, in Claim 21, delete "though" and insert -- through --, therefor.

In column 10, line 23, in Claim 21, delete "though" and insert -- through --, therefor.

In column 10, line 24, in Claim 21, delete "opening," and insert -- opening --, therefor.

Signed and Sealed this

Twenty-third Day of September, 2008

JON W. DUDAS
*Director of the United States Patent and Trademark Office*